United States Patent
Hermann et al.

(10) Patent No.: US 8,382,742 B2
(45) Date of Patent: Feb. 26, 2013

(54) SURGICAL INSTRUMENT

(75) Inventors: Reiner Hermann, Fridingen (DE); Olaf Hegemann, Tuebingen (DE); Theodor Lutze, Balgheim (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/304,847

(22) Filed: Nov. 28, 2011

(65) Prior Publication Data

US 2012/0143175 A1 Jun. 7, 2012

Related U.S. Application Data

(63) Continuation of application No. PCT/EP2010/055397, filed on Apr. 22, 2010.

(30) Foreign Application Priority Data

May 29, 2009 (DE) .......................... 10 2009 024 242
Sep. 14, 2009 (DE) .......................... 10 2009 042 491

(51) Int. Cl.
*A61B 17/00* (2006.01)
(52) U.S. Cl. ........................................... 606/1; 606/130
(58) Field of Classification Search .................. 606/1.13
See application file for complete search history.

(56) References Cited

U.S. PATENT DOCUMENTS

| | | | |
|---|---|---|---|
| 338,310 A | 3/1886 | Smith | |
| 2,515,365 A | 7/1950 | Zublin | |
| 2,694,549 A | 11/1954 | James | |
| 2,712,436 A | 7/1955 | McCune et al. | |
| 2,739,089 A | 3/1956 | Hageltorn | |
| 3,096,962 A | 7/1963 | Meijs | |
| 3,190,286 A | 6/1965 | Stokes | |
| 3,625,200 A | 12/1971 | Muller | |
| 3,674,014 A | 7/1972 | Tillander | |
| 4,328,839 A | 5/1982 | Lyons et al. | |
| 4,600,037 A | 7/1986 | Hatten | |
| 4,706,659 A | 11/1987 | Matthews et al. | |
| 4,790,294 A | 12/1988 | Allred, III et al. | |
| 4,955,384 A | 9/1990 | Taylor et al. | |
| 5,152,744 A | 10/1992 | Krause et al. | |
| 5,179,934 A | 1/1993 | Nagayoshi et al. | |
| 5,437,630 A | 8/1995 | Daniel et al. | |
| 5,695,513 A | 12/1997 | Johnson et al. | |
| 5,755,731 A | 5/1998 | Grinberg | |
| 5,807,241 A | 9/1998 | Heimberger | |
| 5,833,692 A | 11/1998 | Cesarini et al. | |
| 5,921,956 A | 7/1999 | Grinberg et al. | |
| 6,053,922 A | 4/2000 | Krause et al. | |

(Continued)

FOREIGN PATENT DOCUMENTS

| | | |
|---|---|---|
| CH | 119033 | 4/1927 |
| DE | 40 02 449 | 8/1990 |

(Continued)

*Primary Examiner* — Henry M Johnson, III
(74) *Attorney, Agent, or Firm* — Lipsitz & McAllister, LLC

(57) ABSTRACT

A surgical instrument is provided having proximal and distal end sections and a central section extending therebetween. An hollow outer shaft extends from the proximal to the distal end section. A drive element is rotatably mounted in the outer shaft and a tool is coupled to the drive element at the distal end section. The drive element comprises a flexible section arranged between the proximal and distal end sections which consists of a plurality of ring segments each of which has a first and a second end region. The first end region comprises projections which protrude in the axial direction and the second end region comprises recesses for accommodating the projections. The ring segments intermesh in an articulated manner by means of the projections and recesses. The outer shaft comprises an articulation zone which connects the distal end section and the central section together in an articulated manner.

25 Claims, 9 Drawing Sheets

U.S. PATENT DOCUMENTS

| | | |
|---|---|---|
| 6,132,448 A | 10/2000 | Perez et al. |
| 6,352,531 B1 | 3/2002 | O'Connor et al. |
| 6,409,728 B1 | 6/2002 | Ehr et al. |
| 6,447,518 B1 | 9/2002 | Krause et al. |
| 6,817,974 B2 | 11/2004 | Cooper et al. |
| 6,921,397 B2 | 7/2005 | Corcoran et al. |
| 7,090,683 B2 | 8/2006 | Brock et al. |
| 7,105,003 B2 | 9/2006 | Hiltebrandt |
| 7,608,083 B2 | 10/2009 | Lee et al. |
| 2002/0032368 A1 | 3/2002 | Takase |
| 2004/0102772 A1 | 5/2004 | Baxter et al. |
| 2005/0096694 A1 | 5/2005 | Lee |
| 2005/0216018 A1 | 9/2005 | Sennett |
| 2005/0216033 A1 | 9/2005 | Lee et al. |
| 2006/0178556 A1 | 8/2006 | Hasser et al. |
| 2007/0010823 A1 | 1/2007 | Kucklick |
| 2007/0118135 A1 | 5/2007 | Mansmann |
| 2007/0219539 A1 | 9/2007 | Efinger et al. |
| 2007/0282371 A1 | 12/2007 | Lee et al. |
| 2008/0077146 A1 | 3/2008 | Pernsteiner et al. |
| 2008/0234545 A1 | 9/2008 | Breedveld et al. |
| 2010/0151161 A1 | 6/2010 | Da Rolo |
| 2010/0286694 A1 | 11/2010 | Rio et al. |
| 2011/0004157 A1 | 1/2011 | Dewaele et al. |
| 2011/0034764 A1 | 2/2011 | Verbeek |

FOREIGN PATENT DOCUMENTS

| | | |
|---|---|---|
| DE | 695 17 463 | 3/2001 |
| DE | 10 2004 046 539 | 4/2006 |
| DE | 20 2009 007 979 | 9/2009 |
| DE | 20 2009 012 795 | 2/2010 |
| EP | 0 445 918 | 9/1991 |
| EP | 0 626 604 | 11/1994 |
| EP | 0 677 276 | 6/2000 |
| EP | 0 986 989 | 1/2002 |
| EP | 1 243 283 | 9/2002 |
| EP | 0 840 572 | 10/2004 |
| EP | 0 764 423 | 3/2010 |
| WO | 93/13713 | 7/1993 |
| WO | 99/15090 | 4/1999 |
| WO | 2005/067785 | 7/2005 |
| WO | 2006/113216 | 10/2006 |
| WO | 2007/039875 | 4/2007 |
| WO | 2007/146842 | 12/2007 |
| WO | 2009/088430 | 7/2009 |
| WO | 2009/098244 | 8/2009 |
| WO | 2009/112060 | 9/2009 |
| WO | WO 2011/162853 | 12/2011 |

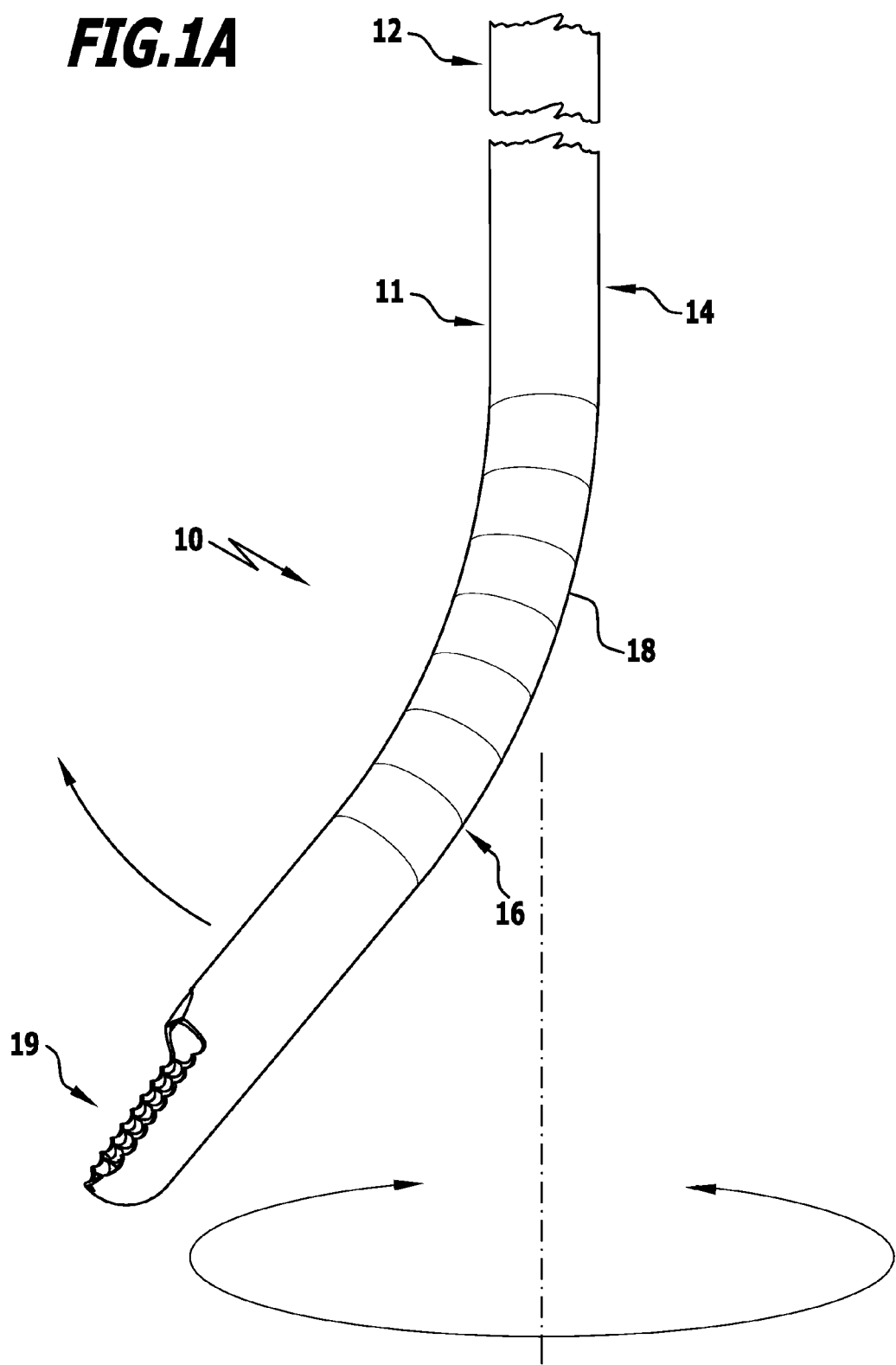

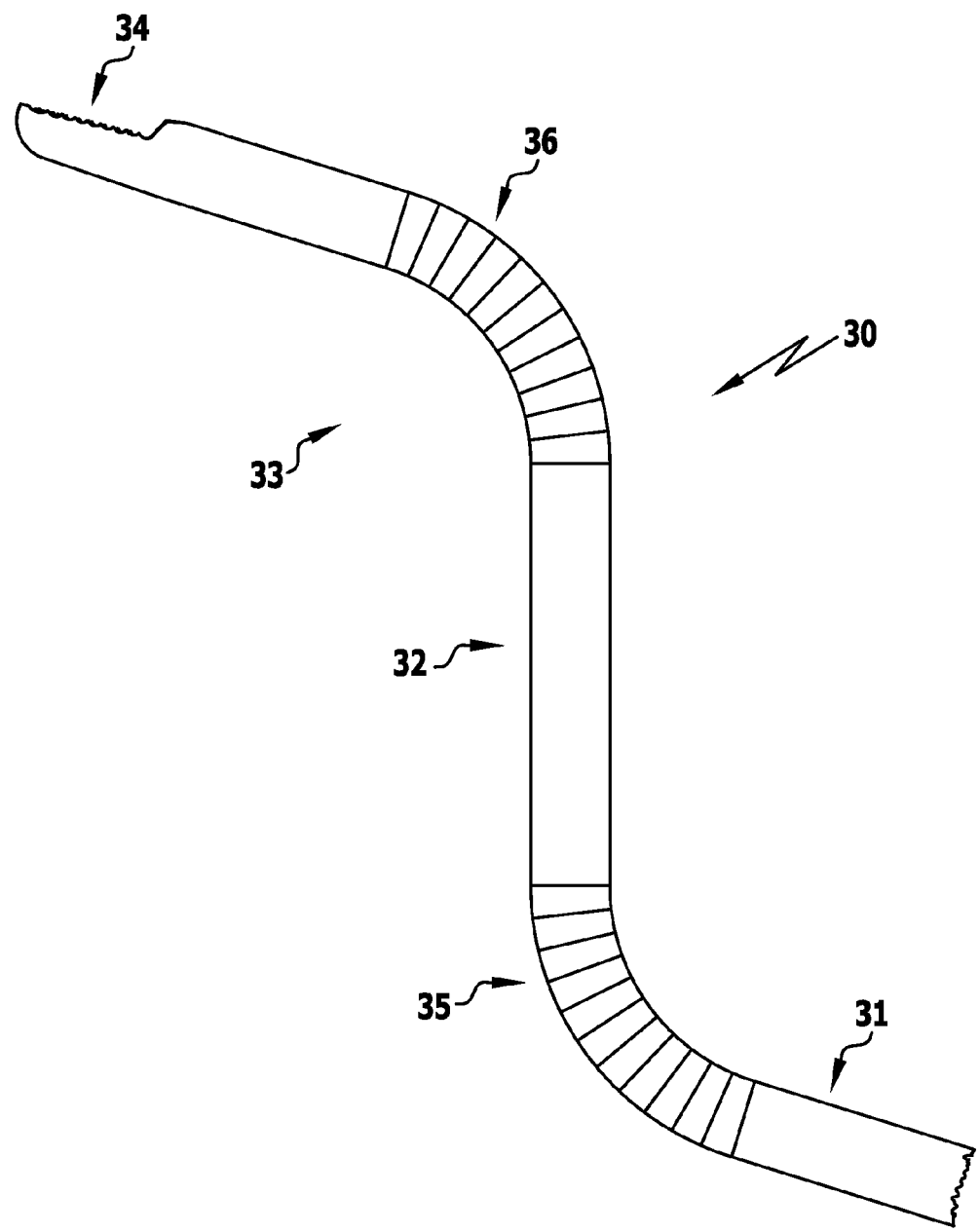

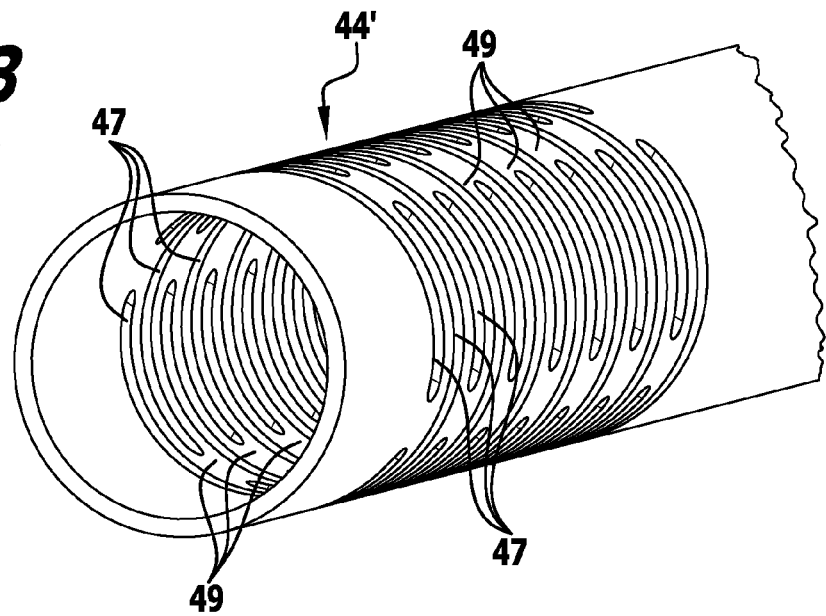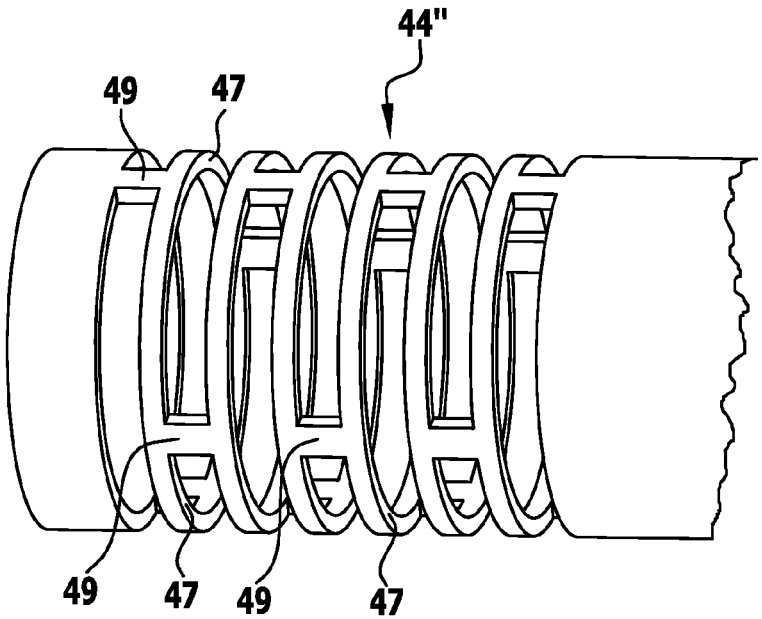

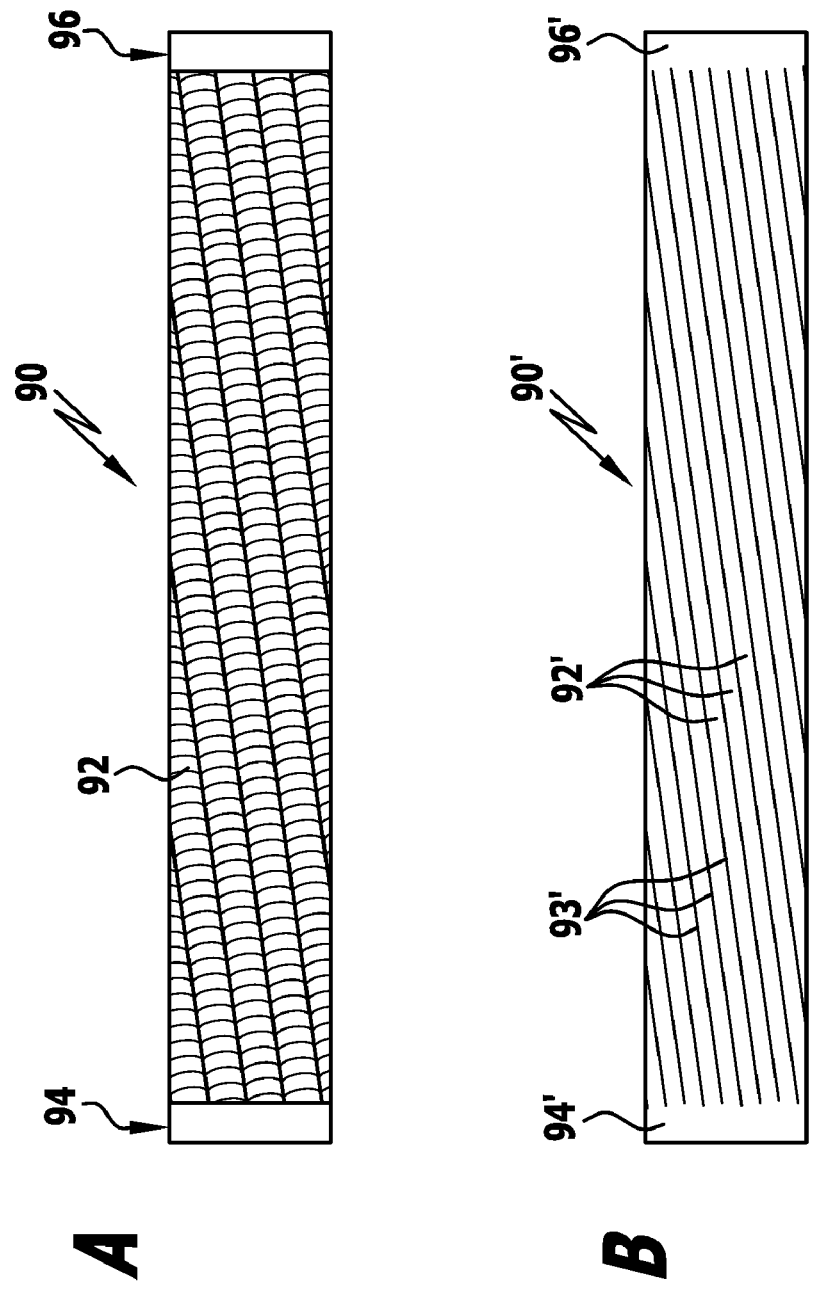

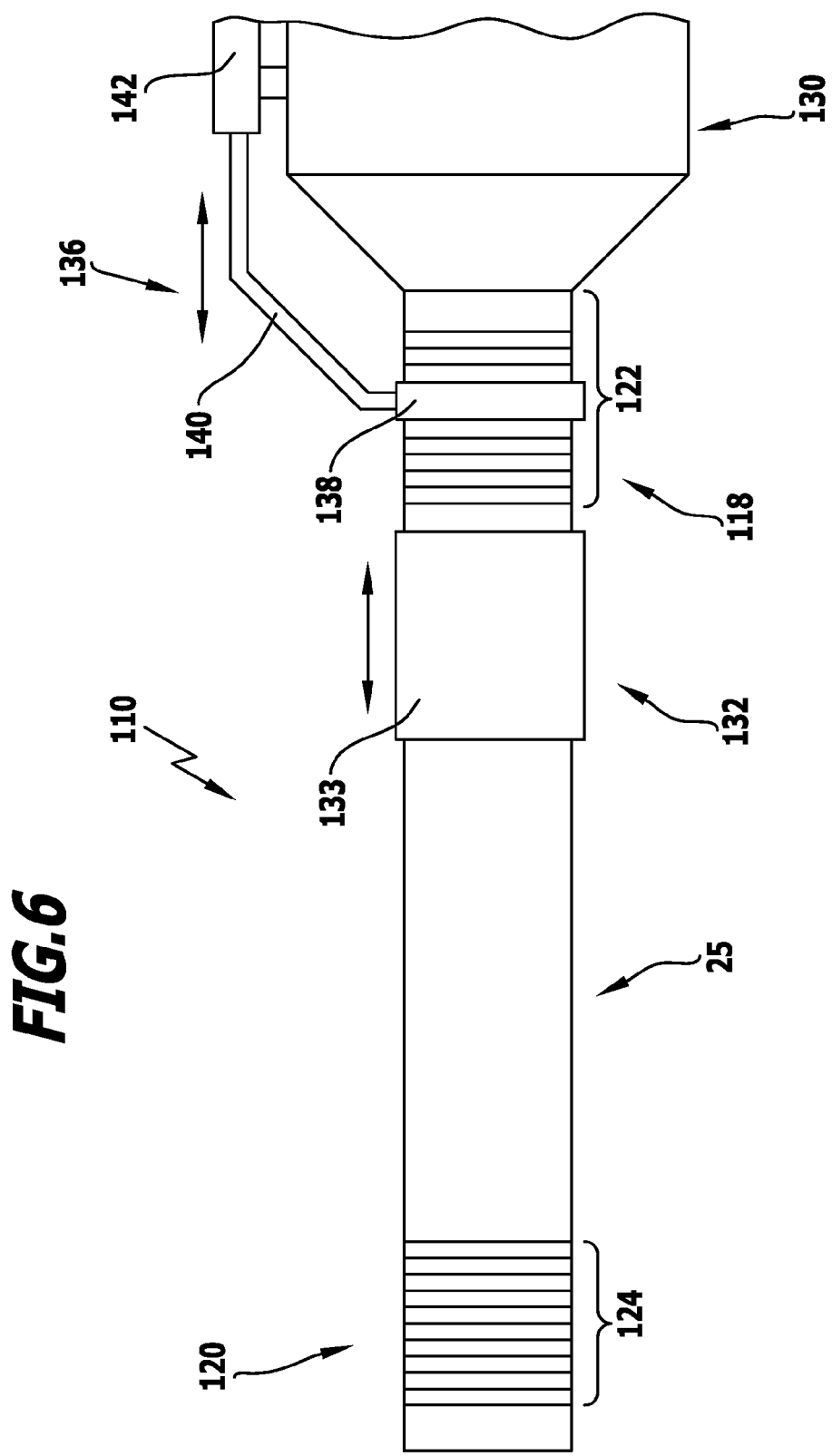

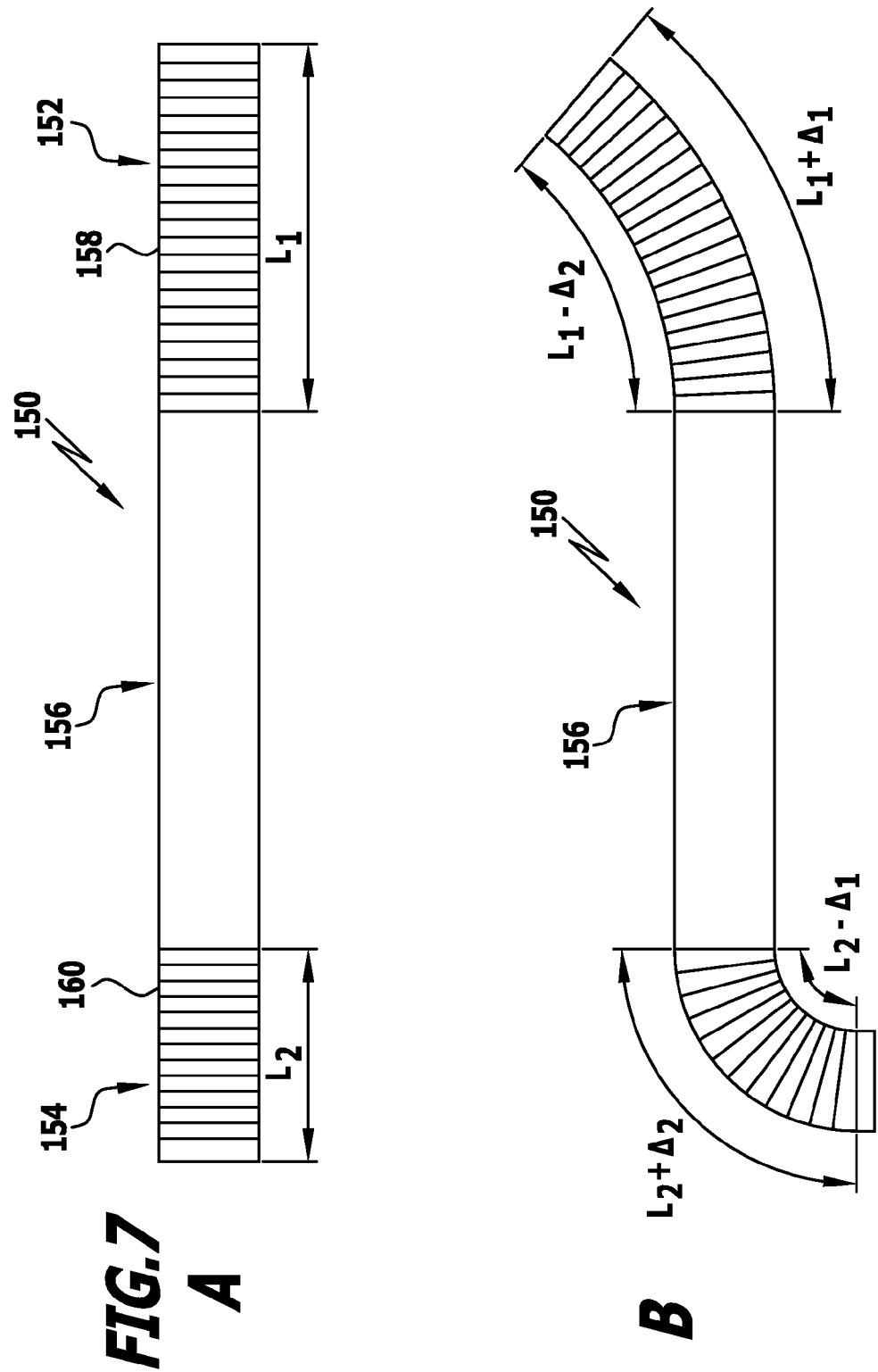

SURGICAL INSTRUMENT

This application is a continuation of international application number PCT/EP2010/055397 filed on Apr. 22, 2010 and claims the benefit of German application number 10 2009 024 242.2 filed on May 29, 2009 and German application number 10 2009 042 491.1 filed on Sep. 14, 2009.

The present disclosure relates to the subject matter disclosed in international application number PCT/EP2010/055397 of Apr. 22, 2010 and German applications number 10 2009 024 242.2 of May 29, 2009 and number 10 2009 042 491.1 of Sep. 14, 2009, which are incorporated herein by reference in their entirety and for all purposes.

BACKGROUND OF THE INVENTION

The invention relates to a surgical instrument for minimally invasive surgical operations comprising a tool coupled to a drive element at a so-called distal end of a shaft. Such instruments are frequently used as so-called shavers.

Surgical instruments of this type have a proximal and also a distal end section together with a central section extending therebetween. An elongated hollow outer shaft, a frequently hollow, cylindrical drive element which is rotatably mounted in the outer shaft and also a cutting, abrading or milling tool which is arranged at the distal end section of the instrument and coupled to the drive element form the essential components of these instruments.

Besides instruments of a linear nature, surgical instruments are also known wherein the distal end region is bent or cranked in order to enable the surgical instrument to reach less easily accessible working positions and generally, to enlarge the working area of the instrument.

In this connection, it is known to provide the drive element with a flexible section between the proximal and distal end section, wherein said flexible section comprises a plurality of ring segments each of which has a first and a second end region in the axial direction, wherein the first end region comprises two or more projections protruding in the axial direction and the second end region has two or more recesses for accommodating the projections and the ring segments intermesh by way of the projections and recesses in articulated manner.

Surgical instruments of this type are known from EP 0 677 276 B1 for example, wherein the flexible section permits the torque to be effectively transmitted from the proximal end section of the drive element to the distal end section and thus to the tool which is attached there.

Since the shaver typically serves for the removal of body tissue, the channel through the interior of the shaft and the (hollow cylindrical) drive element is used for sucking out the removed bits of tissue.

A disadvantage of these known instruments is that the manufacturing process, and particularly the assembly of the flexible section is a complex matter because the flexible section is only loosely composed of a plurality of ring segments so that, not just during the manufacturing process, but also when disassembling the drive element and withdrawing it from the hollow cylindrical outer shaft, ring segments can get lost, especially too in the operating room.

Another shaver which follows this principle for the construction of the drive element utilising loosely intermeshed ring segments in the flexible section is known from DE 10 2004 046 539 A1.

Another starting point was chosen in EP 0 986 989 B1, wherein the flexible section is formed by a hollow cylindrical element in which the wall thereof is slit in helical manner in the radial direction, whereby alternating teeth and indentations alternate in meandering manner along the helical line and intermesh so that the turns then hold together in the axial direction.

A disadvantage of this solution is that it is considerably less flexible and that fatigue fractures frequently occur due to the alternating bending stresses arising when the shaft is rotating. It would of course be possible to use a reciprocating drive with this instrument, but this can be driven at high rotational speeds in one direction of rotation only.

The object of the invention is to develop a surgical instrument of the type described hereinabove in such a way as to make it more reliable especially when operating at high rotational speeds whilst minimising the expenditure on the manufacturing process. A further aspect lies in the provision of an instrument which is employable in a multiplicity of different work situations.

SUMMARY OF THE INVENTION

In accordance with the invention, this object is achieved in the case of a surgical instrument in that the ring segments are connected together in interlocking manner in the axial and/or radial direction by the projections and recesses, and in that the outer shaft comprises an articulation zone which is arranged in the vicinity of the distal end section of the instrument and connects the distal end section and the central section of the instrument together in articulated manner, whereby the length of the flexible section of the drive element in the axial direction corresponds at least substantially to the length of the articulation zone of the outer shaft in the axial direction.

Due to the interlocking of the projections and recesses in the axial and/or radial direction, preferably in the axial and the radial direction, the process of handling the drive element is made considerably easier during the manufacturing process, the assembling process and also any subsequent disassembly process. The articulated connection of the ring segments in the flexible section is nevertheless ensured.

If the ring segments are provided with more than two projections and recesses, two or more axes of articulation can be realized per pair of segments.

Due to the formation of an articulation zone in the distal end section, the latter is connected to the central section in articulated manner. The instrument can be selectively operated with the central section and the distal end section aligned in a straight line or in a multiplicity of configurations which are offset to a greater or lesser degree and are adjustable by the operating surgeon and which, in particular, are also changeable even when working with the instrument.

The interlocking of the ring segments in the axial or radial direction decreases the risk of losing individual ring segments to a considerably extent, that is to say, if such loss is not excluded in advance by the preferred axially and radially interlocking process.

Due to the interlocking process in the axial and/or radial direction, the mutual positioning of the bordering ring segments can be predetermined with such great precision that high rotational speeds can also be realized in both possible drive directions.

The interlocking process in the axial direction can be improved by the use of more than two projections and recesses.

Typically, the projections and recesses are arranged at regular intervals in the circumferential direction of the respective ring segment. This ensures uniform loading of the ring segments during the transmission of the drive forces and thus leads to as long a life span as possible.

In accordance with one embodiment of the present invention, the number of projections and recesses is selected to be an odd number, this thereby resulting in an interlocking arrangement in the radial direction without the need for further measures especially in the case where the projections and recesses are disposed at regular intervals around the periphery of the respective ring segment.

In addition or as an alternative thereto, the interlocking process in the radial direction can be achieved in that the radially outer sides of the projections extend to a greater extent in the circumferential direction than the radially inner sides thereof and in that, in corresponding manner, the extent of the radially inner sides of the recesses in the circumferential direction is smaller than the corresponding radially outer extent in the corresponding region of the projection engaging in the recess.

By virtue of this measure, an interlocking process in the radial direction can be obtained independently of whether the number of projections and recesses is odd or even.

The interlocking process in the axial direction can be achieved by making the free ends of the projections remote from the ring segment extend to a greater extent in the circumferential direction than is the case at the end thereof adjacent to the ring segment and by making the open end of the recesses extend to a smaller extent in the circumferential direction than the extent in the circumferential direction of the free end of the projection which is engaging in the recess.

If an interlocking process is realised in both the axial direction and the radial direction, then one obtains a drive element which can be handled as a whole without the danger of losing individual parts of the flexible section.

Preferably, such a drive element incorporating a flexible section is so manufactured that initially a one piece hollow cylindrical element is used, in which the contours of the projections and recesses are cut-in with a laser for example. Frequently, the gap produced by the cutting process already suffices for ensuring adequate mutual pivoting of the individual ring segments so that the flexible section of the drive element can produce a bending angle which suffices for the particular application.

If the interlocking feature in the axial direction is already present, then the interlocking process in the radial direction can then be obtained by making the radially outer sides in the axial direction of the projections extend to a greater extent in the longitudinal direction than the radially inner sides thereof and by making the depth in the axial direction of the radially inner sides of the recesses smaller than the length of the radially outer sides of the projections in the axial direction.

In a preferred embodiment of the invention, contact surfaces are provided on the part of the projections in the circumferential direction and correspondingly for the recesses, which are flat. The transmission of the torque can thus be optimised this thereby resulting in less wear and tear and permitting the possibility of very high rotational speeds.

A preferred shape for the projections in the circumferential direction is that of a trapezoid, although it is self evident that shapes differing therefrom also enable one to realise an interlocking function in the axial direction. In correspondence therewith, the recesses are also preferably in the form of a trapezoid in the circumferential direction. This then results in wide flat contact surfaces for the projections and the recesses.

For the purposes of ensuring interlocking in the radial direction, the projections are preferably formed with a trapezoidal cross section as seen in the radial direction, wherein here, the curvatures at the radially outwardly located and radially inwardly located surfaces of the projections are not taken into account in this definition.

In a manner corresponding thereto, it is likewise preferable for the recesses to have a trapezoidal cross section in the radial direction.

As already discussed above, one aspect of the invention consists in developing the surgical instrument mentioned hereinabove in such a way that it is employable in a more flexible manner and has a larger working area. This is achieved by virtue of the articulation zone provided in the distal end section.

The adjustment of the angle setting of the distal end section with respect to the central section is preferably effected by means of a control element. In connection therewith, the deflection of the distal end section caused thereby is preferably reversible.

The surgical instrument in accordance with the invention preferably comprises a control element having two or more longitudinal elements for transferring tensile and/or compressive forces which extend at least substantially from the proximal to the distal end section of the instrument. In connection therewith, the longitudinal elements are arranged at substantially regular angular intervals in the circumferential direction of the instrument.

It is further preferred that the force transmitting longitudinal elements be firmly connected together in the circumferential direction at their proximal and distal ends. In such an embodiment too, the proximal end section preferably comprises an articulation zone.

Due to this design of the surgical instrument, pivotal movements can now be effected at the proximal end section to which pivotal movements at the distal end section then correspond. The coupling of the pivotal movements at the proximal and distal end sections is achieved by the control element and its force transmitting longitudinal elements.

Compared with the instruments of the state of the art, it is now possible in place of the linear configuration or fixed-cranked configuration to have a linear or an adjustable cranked configuration as required, whereby this can be varied within predetermined limits even during surgical treatment in the course of an operation.

If two force transmitting longitudinal elements are used, the pivotal movement is restricted to just one plane. If, however, a plurality of, and in particular four or more, for example, eight force transmitting longitudinal elements are used, then it is possible for the surgical instrument to pivot in two mutually perpendicular planes or even, especially when using eight control elements or more, to pivot in practically any selectable planes.

In connection therewith, the pivotal movements are not restricted to angles of approximately 20°, but can quite easily reach values far exceeding 90°.

In a preferred embodiment of the invention, the instrument incorporates a control element which comprises a hollow cylindrical component wherein the cylinder wall is sub-divided into two or more wall segments at least in the region of a section between the proximal and distal ends, said wall segments forming the force transmitting longitudinal elements.

In this connection, the two or more wall segments can be firmly connected together at the distal end of the hollow cylindrical component by an annular collar.

Furthermore, the two or more wall segments can be firmly connected together in the region of the proximal end of the hollow cylindrical component.

It is particularly preferred that the hollow cylindrical component be formed integrally. Here, the handling process involved in assembling the instrument is then particularly simple. Moreover, the one piece component can be manufactured with especial precision in regard to the mutual orientation of the wall segments.

Instruments of this type comprise, in particular, a hollow cylindrical component which is manufactured from a single length of tubing, wherein the sub-division of the cylinder wall into wall segments is preferably effected by means of a laser cutting process.

Particularly suitable materials for manufacturing the control element and in particular the hollow cylindrical component are steel alloys or nitinol.

Furthermore, in a particularly preferred embodiment of the invention, use is made of an internally hollow cylindrical shaft which can be in the form of a drive element for the instrument. The lumen remaining in the interior thereof is thus as large as possible, for example, for carrying away pieces of tissue from the patient being treated which have been stripped off by the tool.

In such a preferred embodiment, the drive element is provided with two flexible sections which, in the assembled state of the instrument, are respectively arranged within the outer shaft in the proximal and distal articulation zones. The effect is thereby achieved that the typically rotatory drive movement can be transferred to the tool attached to the distal end section even when it is in a bent state.

Apart from the cutting, abrading and milling tools mentioned hereinabove, use can also be made of drilling tools, whereby the instrument then has an opening in the axial direction for the insertion of the drilling tool instead of a lateral opening at the distal end thereof.

In order to achieve most effective transmission of the torque in this case, the drive element is formed such that it is substantially torsionally stiff.

In order to prevent twisting of the instrument and to accommodate reaction forces occurring when the tool is in operation, the outer shaft is also preferably formed such that it is torsionally stiff. Any twisting of the instrument would have the consequence that the instrument would move away from its respective intended working position, an effect which could lead to considerable complications in the case of operations that have to be performed with great precision.

In a further embodiment of the present invention, the articulation zones are formed in a resiliently bendable manner so that the surgical instrument would then be restored to its straight-line form should the forces enforcing a pivotal movement at the proximal end be discontinued.

In a variant of the present invention, the force transmitting longitudinal elements are arranged in such a way that they are mutually laterally spaced so that they will not rub against one another during the pivotal movement whereby the pivotal movement can be effected with a minimum amount of force.

Alternatively, a respective spacer can be arranged between the laterally spaced longitudinal elements so that the position of the longitudinal elements in the circumferential direction will remain substantially unchanged even when larger forces have to be applied for the purposes of executing the pivotal movement.

Alternatively, provision may be made for the force transmitting longitudinal elements to be arranged in such a way that they are at least partially in direct contact with one another along the longitudinal direction. Here too it is ensured that the longitudinal elements will also remain in their positions as seen in the circumferential direction even when force is being applied so that precise control of the pivotal movement of the distal end can thus be obtained.

It is also preferred that the force transmitting longitudinal elements be guided in the radial direction by the outer and the inner shaft, this thereby leading to a further improvement in the accuracy of the pivotal movement that is being implemented at the distal end.

In accordance with a further embodiment of the present invention, provision may be made in the case of the control element being used in accordance with the invention, for the distal ends of the longitudinal elements to be fixed in angular positions in the circumferential direction which are different from the angular positions in which the respectively associated proximal ends are fixed.

This permits the pivotal movements of the distal end to occur in a plane other than that in which the pivotal movement of the proximal end is taking place.

The angular difference at which the angular positions of the distal and the proximal ends of a longitudinal element are fixed can fall within a range of approximately 10° to approximately 350°. In particular, differences in the angular intervals at the proximal and distal ends within the range of approximately 45° to approximately 315° are of interest, more preferably, within the range of approximately 150° to approximately 210°.

In order to achieve this, at least sections of the force transmitting longitudinal elements are preferably arranged helically.

In view of the typical length of a surgical instrument and the length of the longitudinal elements resulting therefrom and the simultaneously relatively small diameter, there results an angular positioning of the longitudinal elements along their helical path which deviates to a very small extent from the axial direction of the instrument. This ensures that the instrument can be handled in a reliable manner and also means, in particular, that the pivotal movement of the distal end can be effected in a predictable and angularly precise manner even when there is a very large angular displacement of 180° for example.

In a further embodiment of the invention, provision may be made for the force transmitting longitudinal elements to be arranged in such a way that they are aligned substantially in parallel with the longitudinal axis of the instrument in the vicinity of the proximal and/or distal end sections.

Alternatively, one or more sections could also be arranged such that they are parallel to the longitudinal direction of the instrument.

Here too, in view of the typical length of the requisite control element which is usually more than 10 cm and a typical diameter of the instrument of just a few millimeters, this results in an extremely high helical pitch or, differently expressed, a very small deviation from the parallelism to the longitudinal direction of the instrument which amounts to just a few angular degrees down to a fraction of an angular degree.

In accordance with a variant of the instrument in accordance with the invention, the force transmitting longitudinal elements are in the form of cables or wires.

In another variant, the force transmitting longitudinal elements have a banana shaped cross section.

As already explained before, in a particularly preferred embodiment, the force transmitting longitudinal elements are in the form of a hollow cylindrical component wherein the cylinder wall is slotted over the greater part of its length, and in particular, over virtually the entire length thereof in the axial direction for the purposes of producing the force transmitting longitudinal elements by means of a laser cutting process for example. In connection therewith, the longitudinal elements are formed by cylinder wall segments having a cross section in the form of a circular arc.

Preferably, the cross section of the wall segments is in the form of a circular arc which corresponds to an arc angle of approximately 20° or more, and in particular, of 30° or more.

The number of wall segments preferably lies within a range of 4 to 16, more preferably, within a range of 6 to 12.

As measured in angular degrees, the mutual spacing of the wall segments in the circumferential direction (this corresponds to the slot width) preferably amounts to approximately 2° to 15°, more preferably, to approximately 4° to approximately 8°.

The slot width resulting from the laser cutting process can be increased if necessary, so that the remaining strip-like wall segments can move with respect to one another in non-contacting manner. Due to the segment-of-a-circle-like cross sections of the longitudinal elements, the non-contacting state of the longitudinal elements is retained within the articulation regions even in the event of a tensile or compressive load; this applies, in particular, for the guidance of the longitudinal elements in the radial direction between an inner and an outer shaft.

The two end regions of the hollow cylindrical element are left unslotted so that the longitudinal elements remain connected together by means of annular collars.

The proximal and distal articulation zones of the instrument can be realised in various ways.

If the inner shaft is used as a drive element, it has in the first place flexible sections within the articulation zones which may be sufficient for the realization of the proximal and distal articulation zones. This means that the end sections of the outer shaft must likewise be correspondingly flexible in order to follow the pivotal movements initiated by the control element.

The resistance to bending of the central section can be ensured by a bending resistant arrangement of the inner and/or outer shaft.

Alternatively, both the inner and the outer shaft can have a proximal and a distal articulation section in the vicinity of the proximal and distal articulation zones, whereby, when using the inner shaft as a drive element, the flexible sections thereof correspond to the respective proximal and distal articulation section.

Preferably, the articulation zones of the outer and/or inner shaft comprise several slots which extend in the circumferential direction and are mutually separated from each other in the circumferential direction or the axial direction by means of wall regions.

It is preferred that a respective wall section should comprise two or more, and in particular three or more slots which are arranged one after the other in the circumferential direction. In connection therewith, the slots are preferably arranged at equal distances from each other in the circumferential direction.

In the axial direction, the articulation zones of preferred instruments have three or more slots that are arranged adjacent to one another, wherein it is preferred that the adjacent slots be mutually displaced in the circumferential direction. The spacings by which the slots are spaced from each other in the axial direction can be the same or they can vary, thereby enabling the articulation properties and in particular the bending radius to be affected thereby.

Typically, provision is made for the slots to be slots which completely penetrate through the cylinder wall. Satisfactory bending properties can also be obtained however, if the slots do not pass completely through the wall of the shaft, but rather, if they end, in particular, before reaching the inner periphery. Consequently, the wall of the shaft as a whole remains closed, this being a desirable feature in some applications especially in the case of the outer shaft.

A preferred geometry for the slots is obtained when the wall surfaces bounding the slots are arranged at an acute angle to the radial direction. Preferably thereby, the opposing wall surfaces of the same slot are mirror-imaged so as to result in a larger slot width at the outer periphery of a shaft than there is adjacent to the inner periphery.

Slots spaced from each other in the axial direction preferably overlap in the circumferential direction, arranged mutually displaced, however, so as to result in a regular arrangement of the slots.

In connection therewith, the wall surfaces of the slots can be inclined to the axial direction at an angle which differs from 90° so that the width of the slots at the outer periphery is larger than at the inner periphery of the outer shaft. Consequently, adequately large pivotal angles can be realised even when the slot widths are small without the need to increase the number of the slots or having to extend the articulation region over a greater axial length.

Whereas in many cases the proximal and the distal articulation zones are alike and in particular, extend by the same amount in the longitudinal direction of the instrument, this is not absolutely necessary.

In particular, provision may be made for the proximal and the distal articulation zones to be different and in particular too, to be of different lengths. As a consequence thereof for example, the effect can be achieved that a particular pivotal movement of the proximal articulation zone will result in a smaller or enhanced pivotal movement at the distal end section of the instrument.

In particular, provision may be made for the pivotal movement of the proximal and/or distal articulation zone to be adjustable. This can be effected for example by varying the extent of the proximal and/or the distal articulation zone whereby the pivotal characteristics of the two articulation zones are mutually altered.

In particular, provision may be made for the instrument to comprise a holding device with the aid of which parts of one of the articulation zones are fixable in bending resistant manner with respect to the central section or to a functional unit adjoined to the proximal or distal end section of the instrument.

Thus, in one variant of the instrument in accordance with the invention, the holding device may comprise a bending resistant sleeve which is displaceable in parallel with the longitudinal axis of the bending resistant central section. The length of the proximal and/or distal end section and the articulation zone provided there can be affected in dependence upon the position of the sleeve in the longitudinal direction relative to the central section, and hence the pivotal characteristics thereof can likewise be affected.

Preferably thereby, the bending resistant sleeve is arranged on the outer periphery of the bending resistant shaft so that not only is the lumen of the control device unaffected, but also the position of the sleeve is variable in a simple manner and in particular, it is also fixable.

In accordance with another variant, the holding device on the functional unit, which is coupled to the proximal end of the control device, can comprise a supporting holding element. In this way, the pivotal characteristics of the articulation zone can be affected from the proximal end.

In accordance with a further variant of the instrument in accordance with the invention, the holding device is positionable and in particular too it is fixable in a predetermined position. This thereby gives rise to the possibility of adjusting the mutual pivotal characteristics of the distal and proximal end sections in advance in a repeatable and precisely predictable manner or of readjusting them.

These and further advantages of the invention are explained in yet more detail hereinafter with the aid of the drawings.

BRIEF DESCRIPTION OF THE DRAWINGS

FIG. 1A a perspective illustration of a surgical instrument in accordance with the invention in the form of a shaver;

FIG. 2 a further embodiment of the instrument in accordance with the invention;

FIGS. 4A and B alternative embodiments of a control element for the surgical instrument in accordance with the invention depicted in FIG. 3B;

FIG. 6 a schematic illustration of a first development of the instrument in accordance with the invention depicted in FIG. 2; and FIGS. 7A and B a schematic illustration of a second development of the surgical instrument in accordance with the invention depicted in FIG. 2.

DETAILED DESCRIPTION OF THE DRAWINGS

Figure 1B:
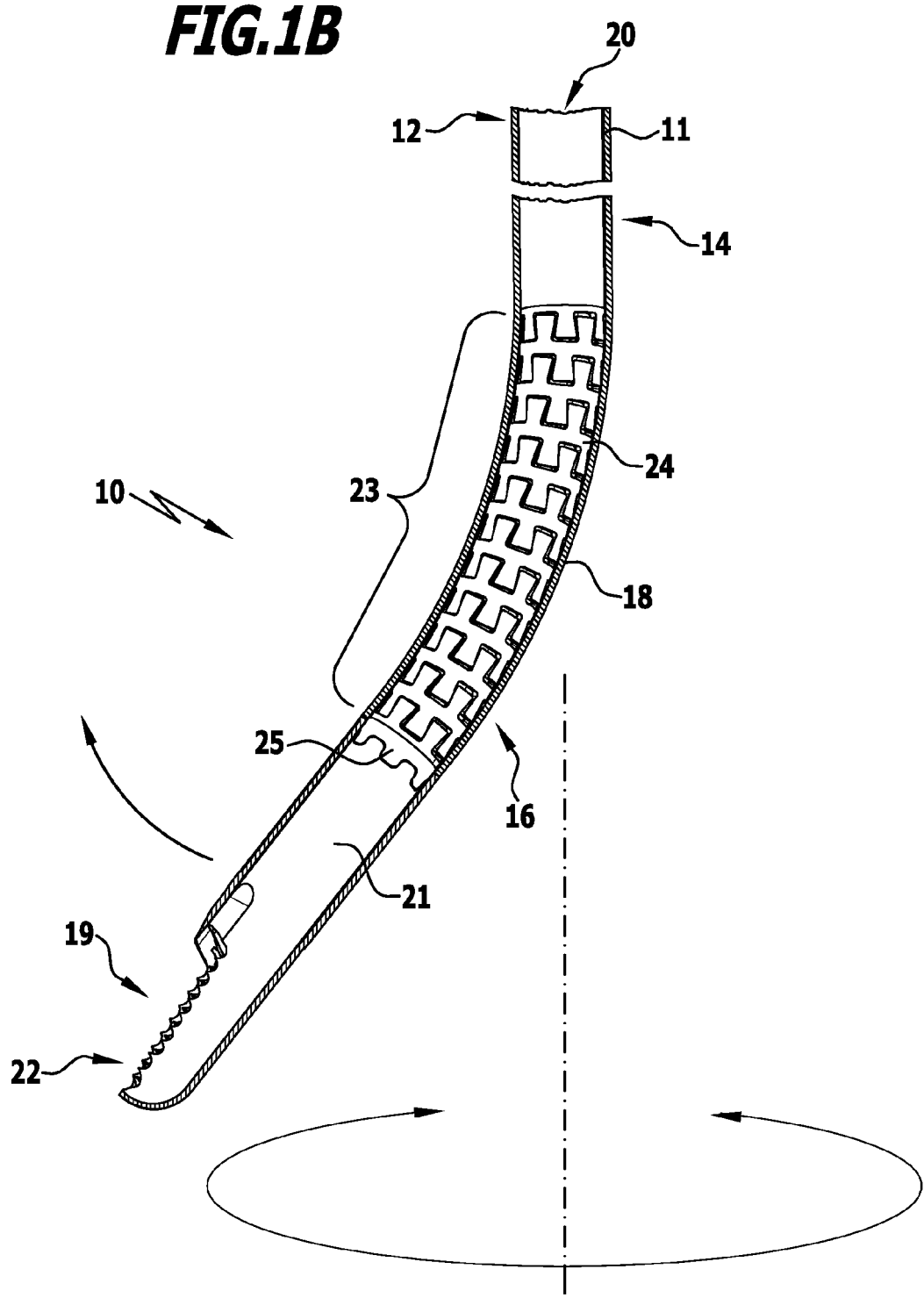
FIG. 1B a sectional view of the shaver depicted in FIG. 1A.

FIG. 1A shows a surgical instrument in accordance with the invention in the form of a shaver 10 having a hollow cylindrical outer shaft 11 which is divided into a proximal end section 12, a straight, bending resistant central section 14 and a slightly bent distal end section 16 incorporating an articulation zone 18, a tool 19, a boring, cutting, abrading or milling tool for example being attached thereto, or in particular, being formed thereon.

The angle at which the distal end section 16 departs from the longitudinal direction of the central section 14 of the instrument 10 is variable due to the articulation zone 18. This makes working in difficult-to-access working positions considerably easier.

The instrument can cover an additional working area, which is significantly more extensive compared with the previously known linear implementation of the instrument, by rotating about the longitudinal axis of the central section 14 which is typically in the form of a trocar.

A rotatably mounted, preferably hollow cylindrical drive element 20 is accommodated in the hollow cylindrical shaft 11.

A tool 22 is coupled to the distal end 21 of the drive element 20, said tool having a lateral opening in like manner to the outer shaft 11. As is evident from FIG. 1B, the edges of the openings are ground and provided with cutting edges. Once the drive element 20 is set into rotary motion, tissue parts reaching the vicinity of the lateral openings are then separated off by the cutting edges at the edges of the openings and can be sucked out via the remaining interior space of the hollow cylindrical drive element 20 by means of negative pressure.

At the distal end section 16 of the shaver 10, i.e. in the vicinity of the articulation zone 18, the hollow cylindrical drive element 20 changes from a one-piece or rigid hollow cylindrical part into a hollow cylindrical flexible section 23 which is formed by a number of ring segments 24 that will be described in greater detail hereinafter with reference to FIG. 5.

The distal end of the drive element 20 typically ends with a coupling piece 25 onto which a releasably-engaging tool, the milling tool 22 in particular, can be coupled.

After suffering from wear and tear for example, the milling tool 22 can thus be exchanged in a simple manner and be replaced by a new or, as required, by other tools. Alternatively, the tool 22 can be rigidly and captively connected to the distal end 21 of the drive element 20.

The setting of the angle at which the distal end section 16 is inclined with respect to the central section can be set by means of known control elements, for example, by Bowden cables. This detail is not shown in FIG. 1B.

In FIGS. 1A and 1B, the distal end of the instrument 10 is shown closed but with a lateral opening therein. If, however, a drilling tool is used in place of a milling tool then, instead of the lateral opening, there is provided an opening in the axial direction which opens up the distal end for the insertion of the drilling tool in the axial direction (not shown).

In accordance with the present invention, a surgical instrument is preferably provided with both a proximal and a distal articulation zone as is shown in FIG. 2 using the example of the shaver 30 and as will be discussed hereinafter.

The shaver 30 in accordance with the invention has a shaft which is divided up into a proximal end section 31, a bending resistant central section 32 and also a distal end section 33.

Attached to or formed on the distal end section 33, there is a tool 34 which can be constructed in a manner corresponding to the one described in DE 10 2004 046 539 A1 for example.

The proximal and the distal end section 31, 33 of the instrument 30 each comprise a respective articulation zone 35, 36 which permits a pivotal movement of the proximal end section 31 that can be converted into a pivotal movement of the distal end section 33 at the articulation section 36 due to a control element of the instrument 30. In consequence, one can work with the shaver 30 of FIG. 2 in both the straight on direction, with a slight bending of the distal end section 33, as well as in the case of significant bending of the distal end section 33, which could be virtually perpendicular for example, this creating a considerably increased working area for the instrument and also allowing access to difficult-to-access working positions.

The construction of the shaver 30 in accordance with the invention will now be described in greater detail with reference to the detailed figures shown in FIGS. 3A to 3C.

Figure 3:
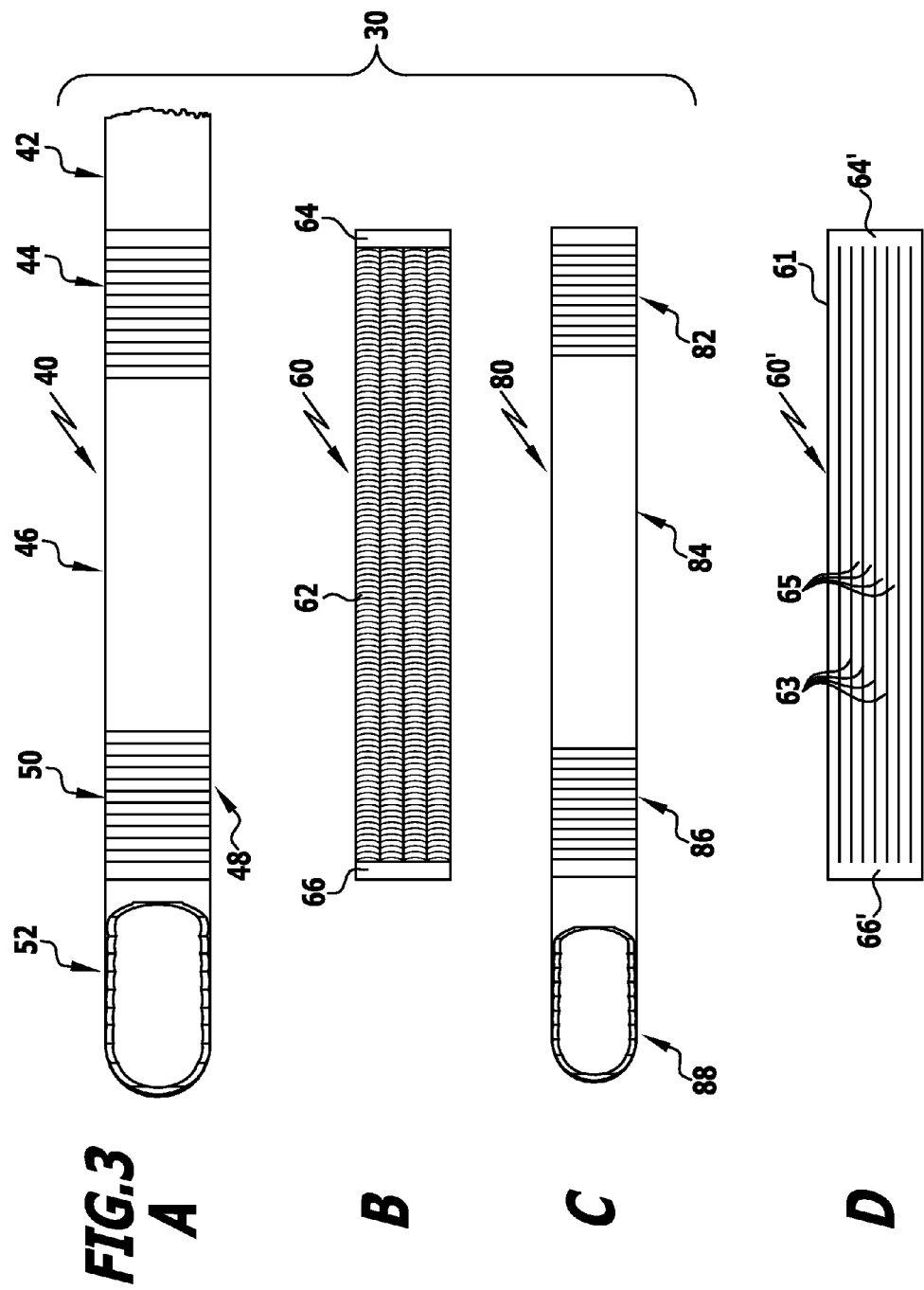
FIGS. 3A, B and C an outer shaft, a control element and also an inner shaft of the instrument in accordance with the invention in accord with FIG. 2.
FIG. 3D an alternative embodiment of the control element depicted in FIG. 3B.
FIGS. 3E and F two alternative embodiments of the articulation sections for the outer shaft depicted in FIG. 3A.

FIG. 3A shows an outer hollow cylindrical shaft 40 having a proximal end section which comprises an end region 42 and a proximal flexible section 44 adjoined thereto, a bending resistant central section 46 that is further adjoined thereto in the direction towards the distal end 52, after which at the distal end section 48 there first follows a flexible section 50 onto which a component of a tool is then attached or formed. In the present case, the component of the tool is formed on the distal end of the outer shaft 40.

A control element 60 which is shown in FIG. 3B is then slid into this outer shaft 40, said control element comprising a multiplicity of, in the present case eight, force transmitting longitudinal elements 62 in the form of cables or wires for example which run parallel to the longitudinal direction of the instrument.

The longitudinal elements 62 are connected together at their proximal and distal ends in the circumferential direction by an annular collar 64, 66. The length of the control element 60 extends from the proximal articulation section 44 of the outer shaft 40 up to the distal articulation section 50 of the outer shaft 40 as is evident from a comparison of the illustrations in FIGS. 3A and 3B.

FIG. 3D shows an alternative embodiment of a control element 60' which is made from a length of one-piece tubing 61 by means of a laser cutting process for example.

The slots 63 formed in the tubing 61 by the laser cutting process extend over almost the entire length of the tubing 61 so that all that remains at the proximal and distal end are unslotted annular collars 64', 66' which interconnect the wall segments 65 functioning as force transmitting longitudinal elements.

Finally, an inner hollow cylindrical shaft 80 is pushed into the interior of the hollow cylindrical control element 60 as is illustrated in FIG. 3C.

The inner shaft 80 also comprises an articulation section or flexible section 82 at the proximal end as well as a bending resistant central section 84 and a distal articulation section or flexible section 86. Attached to the distal articulation section 86, there is a tool component 88 which is arranged in the same position as the tool component at the distal end 52 of the outer shaft 40 after the inner shaft 80 has been pushed through the control element 60 into the outer shaft 40.

In accordance with a preferred embodiment of the invention, provision is made for the inner shaft 80 to function simultaneously as a drive element so that during the rotary motion thereof the tool components 88 and 52 then cooperate and tissue parts coming into contact in this region can be removed by means of a cutting, abrading or milling function for example.

Due to the fact that the inner shaft 80 comprises a free lumen, such tissue parts can be conveyed to the proximal end section 42 via the lumen of the inner shaft 80 and fed away to the exterior.

The design of the articulation sections in the form of the respective flexible sections 44, 50 and 82, 86 of the internal and outer shafts can be quite varied.

FIGS. 3E and 3F show two variants of related designs for the flexible sections, here in the form of the sections 44' and 44". The same type of design is also suitable for the flexible section 50.

Common to the two variants is the use of a slotted structure in the form of circumferential slots 47 in the hollow cylindrical shaft. Preferably, two or more slots that are separated from each other by webs 49 are present along a peripheral line. Since an arrangement of slots along just one peripheral line would only allow a very small pivotal angle, a plurality of axially spaced peripheral lines incorporating slots 47 are present in the typical slotted structures for the articulation zone 44'. It is preferred that the neighbouring slots 47 in the axial direction should be mutually displaced in the circumferential direction thereby giving rise to the possibility of bending in several planes.

There are two slots 47 per peripheral line which are separated from each other by webs 49 in FIG. 3F. In FIG. 3E, there are three slots 47. In both cases, the slotted structure typically consists of a plurality of slots 47 which are arranged along several imaginary peripheral lines that are mutually spaced in the axial direction. The permissible pivotal angle can be pre-defined in a very simple manner and also further properties of an articulation section, e.g. the bending resistance can be adapted to the particular application by the choice of the slotted structure and the number of slots.

FIG. 4A shows an alternative control element 90 in which the force transmitting longitudinal elements 92 are attached to respective proximal and distal annular collars 94, 96 at their proximal and distal ends. In contrast to the control element 60 which is shown in FIG. 3B, the force transmitting longitudinal elements 92 are not arranged in straight lines parallel to the longitudinal axis of the control element 90, but rather, they are arranged along helical lines so that the ends of the longitudinal elements 92 ending at the annular collars 94, 96 are angularly displaced in the circumferential direction. The angular displacement in the circumferential direction in the exemplary embodiment shown in FIG. 4A amounts to approximately 180°, the consequence of which being that a pivotal movement of the proximal end of the instrument leads to a pivotal movement of the distal end section which runs in the same plane of pivoting but in the opposite direction. In place of the S-shape shown in FIG. 2, an instrument having a U-shaped bent configuration is then obtained.

Other angular differences are possible; in the case of an angular displacement of 90° for example, one obtains a pivotal movement of the distal end section which is perpendicular to the pivotal plane of the proximal end section.

FIG. 4B shows a variant of a control element 90' which is formed from a length of one-piece tubing by means of a laser cutting process in a similar manner to that of the control element 60' of FIG. 3D. The wall segments 92' produced thereby are separated from each other by slots 93' and are only connected together in force-locking manner in the vicinity of the annular collars 94', 96'. The advantages of the helical pattern of the wall segments are the same as for the control element 90 with the helically running longitudinal elements 92.

Figure 5:
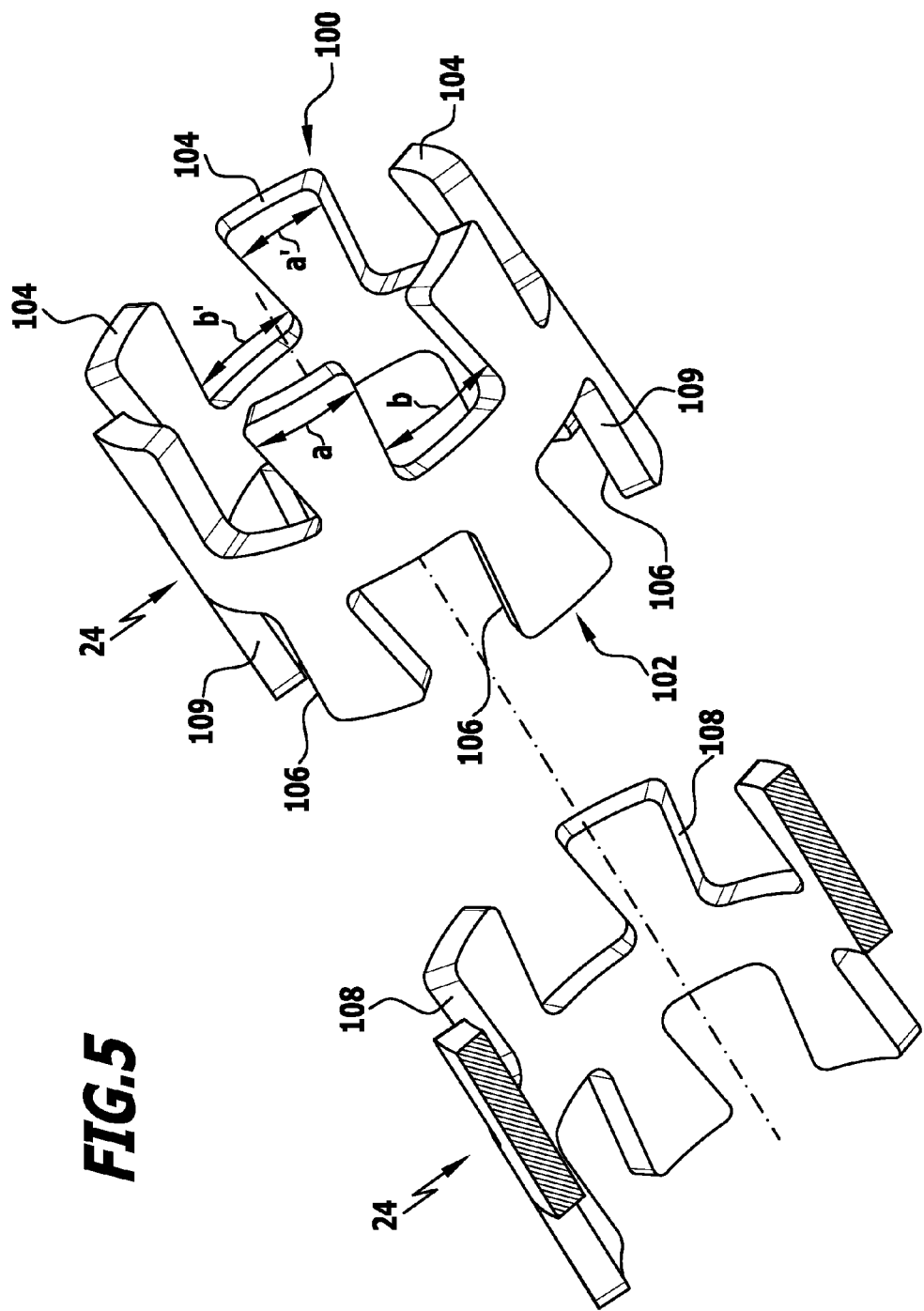
FIG. 5 a detail of a flexible drive element of the instrument depicted in FIG. 1B.

The ring segments 24 of the drive element 20 (FIG. 1B) are illustrated in FIG. 5 in detail and they comprise a first end region 100 in a first axial direction and a second end region 102 in the opposite axial direction. At the first end region thereof, the ring segment 24 has six projections 104 which are arranged on the ring segment 24 and are regularly distributed in the circumferential direction. At the axially opposite end region 102 thereof, the ring segment 24 has shaped indentations or recesses 106 which correspond to the projections 104, whereby the projections and recesses each have the shape of a trapezoid as seen in the circumferential direction, wherein, in the case of the projections 104, the free end thereof in the axial direction extends to a greater extent in the circumferential direction than the end thereof adjacent to the ring segment, whilst in corresponding manner, the inner ends of the recesses 106 extend to a greater extent in the circumferential direction than the outwardly open sections located in the direction of the end region 102. In the case of the ring segments 24 which are shown in detail in FIG. 5, due to the regular geometry of both end regions, there is provided a configuration which is identical right up to the mirror-image arrangement thereof.

Due to the fact that the projections 104 engage in the correspondingly formed recesses 106 with play but nevertheless in positive manner, this results in an axially interlocking arrangement so that the ring segments 24 can be connected to one another in the axial direction and can thus be inserted together into the outer shaft 11 or pulled out together therefrom.

Nevertheless, due to the gap existing between the projections 104 and the recesses 106, there is sufficient play for ensuring an articulated connection of the neighbouring ring segments 24.

The projections 104 and the recesses 106 each have contact surfaces 108, 109 which come into contact with one another, said contact faces being flat and of large surface area in the case of the exemplary embodiment shown in FIG. 5. Consequently, optimal transmission of torque between the individual, successive ring segments is possible.

Due to the multiplicity of projections and recesses 104, 106, there are a plurality of pivotal axes for the connection of two successive ring segments so that the drive element 20 can follow the curved shape of the hollow cylindrical shaft 11.

The plurality of meshing projections and recesses 104, 106 having a trapezoidal configuration gives rise to a particularly secure connection in the axial direction.

In order to enable the drive element 20 and the ring segments 24 forming its flexible section to be handled as a whole in problem-free manner, provision is made for the extent of the free ends of the projections 104 in the circumferential direction at the outer surface (a) to be greater than the corresponding extent thereof at the inner surface (a').

In corresponding manner, the outer and inner peripheries of the recesses 106 are dimensioned with a respective width b and width b', this making it possible for them to interlock in the radial direction as well so that the ring segments 24 are manipulable and connected to one another in captive manner.

Finally, FIG. 6 shows a variant of the present invention in a first further development in which a manipulating device 130 is attached to an instrument 110 at the proximal end section 118 thereof.

As described in connection with FIG. 2, the instrument 110 has proximal and distal articulation zones 122 and 124 that are formed to be of substantially equal length so that, when there is bending of the proximal end section 118 through e.g. 30°, this will result in a corresponding bending of the distal end section 120 likewise through 30°. The direction in which the bending of the distal end section 120 is effected depends on the choice made for the control element which is not shown in detail here and the manner in which the ends of the force transmitting longitudinal elements are fixed, as was described in detail hereinabove.

The instrument 110 shown in FIG. 6 additionally comprises a holding device 132 in the form of a longitudinally displaceable sleeve 133 which is located on the outer shaft of the control device 110 such as to overlap the central section 125.

If one displaces the sleeve 133 towards the proximal end section 118 and lets the sleeve 133 overlap this articulation zone 122, then the articulation zone 122 becomes shorter thereby restricting the maximum bending angle thereof. The permissible bending angle in the region of the distal end section 120 can thus be varied so that, when removing pathological structures using an endoscopic technique for example, a defined working area can be adjusted in the view of an operating surgeon.

FIG. 6 contains an alternative solution to the holding device 132 in the form of the holding device 136 which comprises a longitudinally displaceable ring 138 that is fixed to the manipulating device 130 by means of a doubly cranked bar 140 incorporating a linear guidance mechanism 142. By varying the position of the ring 138 along the section 118, the part of the articulation zone 122 that is available for the bending movement of the proximal end section can be shortened as was explained before in connection with the sleeve 133 thereby again permitting only a restricted bending angle at the distal end section 120. The articulation zones can be constructed as described hereinabove.

Moreover, it is conceivable in both the case of the sleeve 133 and that of the ring 138 for the arrangement to be fixed in a predetermined position, i.e. with a predetermined overlap of the articulation zone so that the adjusted restricted working area at the distal end section 120 is ensured.

On the other hand, it is also conceivable for the sleeve 133 to be displaced towards the distal articulation section 120 whereby a stepped-up i.e. enhanced pivotal movement then takes place in the region of the distal end section 120 when there is a corresponding pivotal movement of the proximal end section 118.

It is likewise conceivable to provide markings for the position of the sleeve 133 or the ring 138 or its linear guidance mechanism 142 so that once a restriction for the angle has been found it can always be accurately re-established on a later occasion.

For the purposes of explaining the above described amplifying effect for the pivotal or bending movement at the distal end, attention is drawn to FIG. 7 which shows an instrument 150 which has a proximal end section 152, a distal end section 154 and also a central section 156 lying therebetween. Whilst the central section 156 is resistant to bending, the proximal and distal end sections 152, 154 each contain an articulation zone 158 or 160 having a respective length $L_1$ and $L_2$ as measured in the axial direction. Here, the length $L_2$ is selected to be shorter than the length $L_1$. FIG. 7A shows the instrument 150 in its basic position in which there are no forces effective on the proximal end section 152.

Should the proximal end region 152 be pivoted out from the axial direction as is made clear in the illustration of FIG. 7B, this then results in the length of the articulation zone 158 being increased to $L_1+\Delta_1$ at the outer radius of the curved end region 152 in the proximal articulation zone 158, whereas it results in a shortened length of $L_1-\Delta_2$ at the inner radius. There are corresponding changes of length for the distal end section 104 with a length at the external radius of $L_2+\Delta_2$ and a length at the inner radius of $L_2-\Delta_1$. Since the lengths $L_1$ and $L_2$ of the articulation zones 158, 160 are different, the inevitable result for the distal end section 154 is that of an enhanced bending movement so as to enable it to follow the variations in length prescribed by the proximal end section.

This effect can, for example, also be used in a restricted proximal working area with proportionately small pivotal movements in order to enable full use to be made of the given radius of pivoting at the distal end and to make as large a working area as possible available at the distal end.

This principle can be used in a variable manner with the present invention, in that the length of one articulation zone in proportion to the other one is varied by a holding device (c.f. FIG. 6).

The invention claimed is:

1. A surgical instrument having a proximal end section and a distal end section and a central section extending therebetween, the instrument comprising:
   an elongated hollow outer shaft extending from the proximal end section to the distal end section,
   a drive element rotatably mounted in the outer shaft,
   a boring, cutting, abrading or milling tool arranged at the distal end section of the instrument which is coupled to the drive element,
   the drive element comprising a flexible section which is arranged between the proximal end section and the distal end section, the flexible section comprising a plurality of ring segments each of which has a first and a second end region in an axial direction, the first end region comprising two or more projections that protrude in the axial direction and the second end region comprising two or more recesses for accommodating the projections, the ring segments intermeshing by means of the projections and recesses in an articulated manner,
   the ring segments being connected together in an interlocking manner in the axial direction and/or a radial direction by the projections and recesses,
   the outer shaft comprising an articulation zone which is arranged in a vicinity of the distal end section and connects the distal end section and the central section together in an articulated manner, a length of the flexible section of the drive element in the axial direction corresponding at least substantially to a length of the articulation zone of the outer shaft in the axial direction, and
a control element with which the distal end section is deflectable with respect to the central section, the control element comprising a hollow cylindrical component arranged between the outer shaft and the drive element, a cylinder wall of the hollow cylindrical component being subdivided into two or more wall segments which form force transmitting longitudinal elements, at least in a region of a section between proximal and distal ends of the hollow cylindrical component.

2. An instrument in accordance with claim 1, wherein the projections and recesses are arranged at regular intervals around a periphery of the respective ring segment.

3. An instrument in accordance with claim 1, wherein there is an odd number of projections and recesses.

4. An instrument in accordance with claim 1, wherein the projections and/or the recesses have a trapezoidal cross section in a circumferential direction.

5. An instrument in accordance with claim 1, wherein the projections and/or recesses have a trapezoidal cross section in the radial direction.

6. An instrument in accordance with claim 1, wherein the projections and the recesses are provided in a circumferential direction with mutually contacting flat contact surfaces.

7. An instrument in accordance with claim 1, wherein two adjacent ring segments form two or more axes of articulation.

8. An instrument in accordance with claim 1, wherein the control element comprises two or more force transmitting longitudinal elements which are arranged such that they are regularly distributed in a circumferential direction of the outer shaft and extend from the proximal end section to the distal end section.

9. An instrument in accordance with claim 8, wherein the outer shaft comprises a second articulation zone in the proximal end section, and the force transmitting longitudinal elements are firmly connected together in the circumferential direction at their respective proximal and distal ends.

10. An instrument in accordance with claim 8, wherein the force transmitting longitudinal elements are in the form of cables or wires.

11. An instrument in accordance with claim 8, wherein the force transmitting longitudinal elements have a banana shaped cross section.

12. An instrument in accordance with claim 8, wherein the force transmitting longitudinal elements are arranged in such a way that they are mutually laterally spaced.

13. An instrument in accordance with claim 12, wherein spacers are arranged between the force transmitting longitudinal elements.

14. An instrument in accordance with claim 8, wherein the control element is formed to be torsion resistant.

15. An instrument in accordance with claim 1, wherein the two or more wall segments are firmly connected together at the distal end of the hollow cylindrical component by an annular collar.

16. An instrument in accordance with claim 1, wherein the two or more wall segments are firmly connected together in a region of the proximal end of the hollow cylindrical component.

17. An instrument in accordance with claim 1, wherein the articulation zone of the outer shaft is bendable in a resilient manner.

18. An instrument in accordance with claim 1, wherein at least one of the articulation zone of the outer shaft and the flexible section of the drive element comprise a wall section in which there are arranged a plurality of mutually spaced slots running in a circumferential direction.

19. An instrument in accordance with claim 1, wherein the outer shaft has a second articulation zone, wherein one of the articulation zones is arranged proximally and the other articulation zone distally on the instrument.

20. An instrument in accordance with claim 1, wherein the drive element is in the form of a hollow cylinder.

21. An instrument in accordance with claim 20, wherein the drive element forms an inner shaft.

22. A surgical instrument having a proximal end section and a distal end section and a central section extending therebetween, the instrument comprising:
an elongated hollow outer shaft extending from the proximal end section to the distal end section,
a drive element rotatably mounted in the outer shaft,
a boring, cutting, abrading or milling tool arranged at the distal end section of the instrument which is coupled to the drive element,
the drive element comprising a flexible section which is arranged between the proximal end section and the distal end section, the flexible section comprising a plurality of ring segments each of which has a first and a second end region in an axial direction, the first end region comprising two or more projections that protrude in the axial direction and the second end region comprising two or more recesses for accommodating the projections, the ring segments intermeshing by means of the projections and recesses in an articulated manner,
the ring segments being connected together in an interlocking manner in the axial direction and/or a radial direction by the projections and recesses,
the outer shaft comprising an articulation zone which is arranged in a vicinity of the distal end section and connects the distal end section and the central section together in an articulated manner, a length of the flexible section of the drive element in the axial direction corresponding at least substantially to a length of the articulation zone of the outer shaft in the axial direction,
a control element with which the distal end section is deflectable with respect to the central section, the control element comprising two or more force transmitting longitudinal elements which are arranged such that they are regularly distributed in a circumferential direction of the outer shaft and extend from the proximal end section to the distal end section, and
an inner hollow cylindrical shaft which guides the force transmitting longitudinal elements in the radial direction and incorporates an articulation zone which is arranged in the longitudinal direction in correspondence with a position of the articulation zone in the vicinity of the distal end section of the outer shaft, the force transmitting longitudinal elements of the control element being arranged between the outer shaft and the inner hollow cylindrical shaft.

23. An instrument in accordance with claim 22, wherein the articulation zone of the inner shaft is of substantially the same length as the articulation zone of the outer shaft.

24. An instrument in accordance with claim 22, wherein the inner shaft is arranged within the drive element.

25. An instrument in accordance with claim 22, wherein the inner shaft is arranged between the drive element and the outer shaft.

* * * * *